United States Patent [19]

Itzel

[11] 4,405,605
[45] Sep. 20, 1983

[54] FUNGICIDAL COMPOSITIONS

[75] Inventor: Hanshelmut Itzel, Gau-Algesheim, Fed. Rep. of Germany

[73] Assignee: Celamerck GmbH & Co., KG, Ingelheim am Rhein, Fed. Rep. of Germany

[21] Appl. No.: 286,693

[22] Filed: Jul. 24, 1981

Related U.S. Application Data

[63] Continuation of Ser. No. 219,246, Dec. 22, 1980.

[30] Foreign Application Priority Data

Oct. 15, 1980 [DE] Fed. Rep. of Germany ....... 2952239

[51] Int. Cl.$^3$ .................... A01N 43/50; A01N 43/48; A01N 25/22
[52] U.S. Cl. .................................. 424/173; 424/176; 424/250; 424/273 R
[58] Field of Search ............ 424/176, 173, 250, 273 R

[56] References Cited

U.S. PATENT DOCUMENTS

| 3,705,939 | 12/1972 | Kleppling et al. | 424/245 |
| 3,717,709 | 2/1973 | Ost et al. | 424/250 |
| 3,912,738 | 10/1975 | Ost et al. | 424/250 |

FOREIGN PATENT DOCUMENTS

| 1022559 | 12/1977 | Canada. | |
| 2521384 | 11/1976 | Fed. Rep. of Germany | 424/250 |
| 1476948 | 6/1977 | United Kingdom. | |

Primary Examiner—Delbert R. Phillips
Assistant Examiner—F. T. Moezie
Attorney, Agent, or Firm—Hammond & Littell, Weissenberger and Muserlian

[57] ABSTRACT

This invention relates to fungicidal compositions comprising triforine and carbendazim as active ingredients, wherein the composition comprises carbendazim suspended in a solution of a triforine in dimethylformamide, N-methylpyrrolidone, or a mixture thereof and contains a stabilizer selected from the group consisting of saccharides, polyethylene glycol, polyvinylpyrrolidone/polyvinylacetate mixtures, and mixtures thereof.

15 Claims, No Drawings

FUNGICIDAL COMPOSITIONS

This is a continuation, of Ser. No. 219,246, filed Dec. 22, 1980.

FIELD OF THE INVENTION

The invention is related to novel fungicidal compositions and their production. More specifically, the invention is related to stabilized fungicidal compositions comprised of triforine and carbendazim.

BACKGROUND OF THE INVENTION

For biological reasons, it is desirable to employ together the two systemic fungicides 1,1'-piperazine-1,4-diyldi-[N-(2,2,2-trichloroethyl)-formamide] and methylbenzimidazole-2-ylcarbamate, also known as triforine and carbendazim, respectively, for control of fungal diseases in plants. Preparations containing both active substances are desired to facilitate better handling of the active substance combinations.

Triforine develops its full activity only if it is used in dissolved form. To obtain good stability of triforine concentrates, they are formulated with addition of salts of dodecyclbenzene sulfonic acid (DBS), in particular, amine salts. Carbendazim is preferably used in the form of wettable powders.

In accordance with the prior art, the problem of producing a combined liquid formulation of the active substances sufficient for practical requirements seemed to be unsolvable. Triforine is sufficiently soluble only in very few solvents. In these solvents, however, the solubility of carbendazim is too low, between 0.7 percent and 0.35 percent at room temperature, to produce solution concentrates. On the other hand, this solubility is too high for assuming that carbendazim solid substance might be processed to a sufficiently stable suspension in these solvents. When such preparations are stored, or shelved, crystal growth due to the Ostwald-ripening would be expected, according to the present level of knowledge. Such crystal growth would make the preparations unfit for use as fungicidal agents.

Carbendazim itself forms soluble DBS salts. Employment of the DBS salt, which salts are, according to German Offenlegungsschrift No. 25 21 284, important for the stability of triforine preparations, increases solubility of the carbendazim. This reduces the chance of impeding the growth of crystals. Also, carbendazim cannot be used directly in form of the soluble DBS salts of carbendazim (German Offenlegungsschrift No. 24 17 008), as these salts are unstable, hydrolyze within a short time, and lead to non-reversible precipitation of carbendazim in large crystals.

In addition, the carbendazim adducts disclosed in German Offenlegungsschrift No. 22 19 174 are unstable in the mixtures with triforine and DBS salts. Furthermore, liquid preparations of carbendazim are disclosed in German Offenlegungsschrift Nos. 19 57 712, 21 54 020, 23 03 757, and 23 54 467 and in Japanese patent application No. 72 40 060. However, these liquid preparations cannot be considered for use in fungicidal compositions with triforine since, for example, metal salts catalyze decomposition of triforine and triforine is insoluble in mineral oils and cannot exhibit fungicidal activity.

OBJECTS OF THE INVENTION

It is an object of the invention to provide novel fungicidal compositions.

It is a further object of the invention to provide a method of using such novel fungicides.

It is yet a further object of the invention to provide fungicidal compositions comprising suspensions of carbendazim and solutions of triforine in dimethylformamide and/or N-methylpyrrolidine, which compositions also comprise saccharides and/or polyethylene glycol and/or mixtures of polyvinylpyrrolidone/polyvinylacetate.

These and other objects of the invention will become more apparent in the discussion below.

DETAILED DESCRIPTION OF THE INVENTION

Applicant has found a practical manner in which to provide stable suspensions of carbendazim in solutions of triforine. Accordingly, Applicant's invention relates to compositions comprising suspensions of carbendazim in solutions of triforine in dimethylformamide and/or N-methylpyrrolidone, optionally having a content of DBS salts, wherein the compositions are stabilized by the addition of saccharides and/or polyethylene glycol (PEG) and/or mixtures of polyvinylpyrrolidone/polyvinylacetate (PVP/PVA). The result is that, on the one hand, the finely dispersed carbendazim does not precipitate in suspensions of this type and, on the other hand, there is only a slight tendency to recrystallize.

The basic formulation comprises a solution of triforine in N-methylpyrrolidine, dimethylformamide, or mixtures of these solvents, whereby the triforine content is from about 1 to 20, preferably from about 5 to 15, percent by weight, based on the total weight of the final composition. The carbendazim content is from about 1 to 40, preferably from about 5 to 15, percent by weight.

The stabilization agents useful according to the invention may be employed alone or in combination. Useful saccharides include oligo- and polysaccharides in quantities of from about 1 to 40, preferably from about 3 to 10, percent by weight, based on the weight of the final composition. Saccharose, maltose, lactose, raffinose, dextrin, starch, and cellulose are examples of suitable saccharides. In general, good stabilization is obtained more easily with polysaccharides than with di- or trisaccharides.

Polyethylene glycols suitable as stabilizers are those having a molecular weight greater than 2000, preferably of from about 6000 to 35,000. The content of polyethylene glycol, including mixtures of polyethylene glycols, in the final formulation amounts to from about 5 to 15, preferably from about 10 to 15, percent by weight.

Polyvinylpyrrolidone and polyvinylacetate are employed in the form of mixtures in the proportion by weight of from about 4:1 to 1:4, preferably from about 1:1 to 2:1. The mixtures are added to the final formulations in quantities of from about 1 to 15, preferably from about 1 to 5, percent by weight.

If a combination of two useful stabilizers according to the invention is employed, it is practical to use combinations of saccharides and PVP/PVA mixtures in a proportion by weight of from about 1:15 to 40:1, preferably from about 5:1 to 10:1, and combinations of saccharides and PEG in a proportion of from about 1:5 to 5:1, preferably from about 2:5 to 1:1. If combinations of three stabilizers are employed, it is advantageous to use mixtures of PEG, saccharides, and PVP/PVA in proportions of from about 1:1:1 to 5:1:1 to 1:5:1 to 5:5:1, that is, in proportions of from about 1-5:1-5:1. Proportions of from about 2:2:1 to 3:3:1 are preferred.

When a combination of two or three stabilizers is used, the combination is present in the final composition in an amount of from about 1 to 25, preferably from about 5 to 20, percent by weight.

The following examples are intended to illustrate the invention and are not to be construed as limiting the invention thereto.

EXAMPLES

EXAMPLE I

Triforine is dissolved, perhaps with further excipients, in a mixture of solvents, PVA/PVP and DBS amine salts. Finely ground saccharide, ground in a pearl or ball mill until the saccharide has a particle size of 5μ, is added to the solution, and then the solution is well chilled. Subsequently, carbendazim is added to the cooled mixture, preferably after the mixture has been subjected to an air jet grinding and substantially no particles remain bigger than 5μ. Then it is dispersed or finely ground in a pearl or ball mill again. The product thus obtained possesses an excellent sedimentation and shelving stability.

EXAMPLE II

Micronized carbendazim, together with polyethylene glycols having an average molecular weight of 6000, is stirred into a solution of triforine and DBS amine salts in dimethylformamide. The mixture thus obtained is ground by means of a pearl or ball mill while being well chilled.

EXAMPLE III

A mixture of polyethylene glycol and saccharide, preferably dextrin, is suspended in dimethylformamide. This suspension is subjected to a wet grinding in a ball mill. A solution of triforine, DBS amine salt, and antifoaming agent, prepared separately, is thoroughly mixed into the mixture. Then, micronized carbendazim is suspended in the mixture.

Using the procedures set forth in Examples I to III, the following testing was performed:

EXAMPLE IV

Stabilization with Polyethylene Glycol

The concentrates prepared had the following composition:

| Component | Amount (percent by weight) |
|---|---|
| Triforine | 10.0 |
| Carbendazim | 10.0 |
| Emulsifier (DBS amine salt) | 10.0 |
| Polyethylene glycol | 10.0 |
| Dimethylformamide | to 100.0 |

Several similar compositions having different polyethylene glycol contents were tested for stability, and the results are set forth in the following table:

TABLE 1

| Sample | Molecular Weight of Polyethylene Glycol | Percent of Supernatant Liquid After 20 Days |
|---|---|---|
| Control | — | 74 |
| A | 6,000 | 0 |
| B | 20,000 | 17 |
| C | 35,000 | 0 |

EXAMPLE V

Stabilization with Saccharides

The concentrated prepared had the following composition:

| Component | Amount (percent by weight) |
|---|---|
| Triforine | 10.0 |
| Carbendazim | 10.0 |
| Emulsifier (DBS amine salt) | 10.0 |
| Saccharide | 3-20 |
| Dimethylformamide | to 100.0 |

Compositions having different saccharide contents were tested for stability, and the results are set forth in the following table:

TABLE 2

| Sample | Saccharide | Concentration of Saccharide (% by wt.) | Percent of Supernatant Liquid After 20 Days |
|---|---|---|---|
| Control | — | — | 74 |
| A | Cane Sugar | 20 | 31 |
| B | Starch | 10 | 12 |
| C | Starch | 20 | 3 |
| D | Cellulose | 3 | 0 |
| E | Dextrin | 10 | 1 |
| F | Dextrin | 15 | 0 |

EXAMPLE VI

Stabilization with Dextrin and PVP/PVA

The concentrates prepared had the following composition:

| Component | Amount (percent by weight) |
|---|---|
| Triforine | 10.0 |
| Carbendazim | 10.0 |
| Triethylamine salt of DBS | 12.0 |
| Antifoam agent | 2.0 |
| Dextrin | 5-15 |
| Mixture of PVP/PVA | 0-5 |
| Dimethylformamide | to 100.0 |

Compositions having different dextrin and PVP/PVA concentrations were tested for stability, and the results are set forth in the following table:

TABLE 3

| Sample | Dextrin (percent by weight) | PVP/PVA (percent by weight) | Percent of Supernatant Liquid After 20 Days |
|---|---|---|---|
| Control | 0 | 0 | 75 |
| A | 5 | 0 | 37 |
| B | 5 | 1 | 28 |
| C | 5 | 5 | 9 |
| D | 10 | 0 | 7 |
| E | 15 | 5 | 0 |

EXAMPLE VII

Stabilization with PEG, Dextrin, and, Optionally, PVP/PVA

Concentrates prepared had the following composition:

| Component | Amount (percent by weight) |
| --- | --- |
| Triforine | 10.0 |
| Carbendazim | 10.0 |
| Polyethylene glycol (MW = 6000) | 5 |
| Dextrin | 0–10 |
| PVP/PVA (30:70) | 0–5 |
| Dimethylformamide | to 100.0 |

Compositions having different stabilizer contents were tested for stability, and the results were as follows:

TABLE 5

| Sample | Polyethylene Glycol (percent by weight) | Dextrin (percent by weight) | PVP/PVA (percent by weight) | Percent of Supernatant Liquid After 20 Days |
| --- | --- | --- | --- | --- |
| A | 5 | 0 | 0 | 10 |
| B | 5 | 2 | 0 | 2 |
| C | 5 | 2 | 2 | 0 |
| D | 5 | 5 | 0 | 0 |
| E | 5 | 5 | 2 | 0 |
| F | 5 | 10 | 0 | 0 |
| G | 5 | 10 | 5 | 0 |

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A fungicidal composition comprising fungicidally effective amounts of triforine and carbendazim as active ingredients, wherein the composition consists essentially of (1) from about 1 to 40 percent by weight, based upon the weight of the total composition, of carbendazim suspended in a solution of from about 1 to 20 percent by weight, based upon the weight of the total composition, of triforine in dimethylformamide, N-methylpyrrolidone, or a mixture thereof; (2) from about 1 to 40 percent by weight, based upon the weight of the total composition, of saccharide or from about 1 to 15 percent by weight, based upon the weight of the total composition, of a polyvinylpyrrolidone/polyvinylacetate mixture, the weight ratio of polyvinylpyrrolidone to polyvinylacetate in the mixture being from about 4:1 to 1:4, or a mixture thereof, as stabilizer; and (3) inert carrier.

2. The composition of claim 1 comprising fungicidally effective amounts of triforine and carbendazim as active ingredients, wherein the composition consists essentially of (1) from about 1 to 40 percent by weight, based upon the weight of the total composition, of carbendazim suspended in a solution of from about 1 to 20 percent by weight, based upon the weight of the total composition, of triforine in dimethylformamide, N-methylpyrrolidone, or a mixture thereof; (2) from about 1 to 40 percent by weight, based upon the weight of the total composition, of dextrin as stabilizer; and (3) inert carrier.

3. The composition of claim 1, wherein the triforine is present in an amount of from about 5 to 15 percent by weight.

4. The composition of claim 1, wherein the carbendazim is present in an amount of from about 5 to 15 percent by weight.

5. The composition of claim 1, wherein the saccharide is present in an amount of from about 3 to 10 percent by weight.

6. The composition of claim 1, wherein the polyvinylpyrrolidone/polyvinylacetate mixture is present in an amount of from about 1 to 5 percent by weight.

7. The composition of claim 1, wherein the polyvinylpyrrolidone/polyvinylacetate weight ratio is from about 1:1 to 2:1.

8. The composition of claim 1, wherein the stabilizer comprises a mixture of saccharide and polyvinylpyrrolidone/polyvinylacetate mixture in a weight ratio of from about 1:15 to 40:1.

9. The composition of claim 8, wherein the weight ratio is from about 5:1 to 10:1.

10. The composition of claim 1 which also contains a dodecylbenzene sulfonic acid salt.

11. The composition of claim 1, wherein the stabilizer is dextrin.

12. The composition of claim 1, wherein the stabilizer is a mixture of dextrin and a polyvinylpyrrolidone/polyvinylacetate mixture.

13. A method for preparing a stabilized fungicidal composition comprising fungicidally effective amounts of triforine and carbendazim as active ingredients which comprises admixing (1) from about 1 to 40 percent by weight, based upon the weight of the total composition, of saccharide or from about 1 to 15 percent by weight, based upon the weight of the total composition, of a polyvinylpyrrolidone/polyvinylacetate mixture, the weight ratio of polyvinylpyrrolidone to polyvinylacetate in the mixture being from about 4:1 to 1:4, or a mixture thereof with (2) from about 1 to 40 percent by weight, based upon the weight of the total composition, of carbendazim suspended in a solution of from about 1 to 20 percent by weight, based upon the weight of the total composition, of triforine in dimethylformamide, N-methylpyrrolidone, or a mixture thereof.

14. The method of claim 13 for preparing a stabilized fungicidal composition comprising fungicidally effective amounts of triforine and carbendazim as active ingredients which comprises admixing (1) from about 1 to 40 percent by weight, based upon the weight of the total composition, of dextrin with (2) from about 1 to 40 percent by weight, based upon the weight of the total composition, of carbendazim suspended in a solution of from about 1 to 20 percent by weight, based upon the weight of the total composition, of triforine in dimethylformamide, N-methylpyrrolidone, or a mixture thereof.

15. The method of controlling downy mildew or fungi leaf diseases which comprises applying to a host an effective amount of a fungicidal composition of claim 1.

* * * * *